(12) United States Patent
Ulert et al.

(10) Patent No.: US 6,576,010 B2
(45) Date of Patent: Jun. 10, 2003

(54) CIRCULAR ARTIFICIAL HEART

(76) Inventors: Izaak A. Ulert, 2929 Post Oak Blvd. Apt. 402, Houston, TX (US) 77056; Meinrich Lang, 43 Winter Wheat Pl., Woodlands, TX (US) 77381

( * ) Notice: Subject to any disclaimer, the term of this patent is extended or adjusted under 35 U.S.C. 154(b) by 0 days.

(21) Appl. No.: 09/909,614

(22) Filed: Jul. 20, 2001

(65) Prior Publication Data

US 2002/0019666 A1 Feb. 14, 2002

Related U.S. Application Data

(60) Provisional application No. 60/219,868, filed on Jul. 20, 2000.

(51) Int. Cl.[7] .................................................. A61M 1/12
(52) U.S. Cl. ........................ 623/3.1; 623/3.11; 623/3.14
(58) Field of Search .................................. 623/3.1, 3.11, 623/3.16, 3.17, 3.28, 3.27, 3.14, 3.19; 600/16, 17

(56) References Cited

U.S. PATENT DOCUMENTS

| | | | | |
|---|---|---|---|---|
| 3,733,616 A | * | 5/1973 | Willis, Jr. .................. | 623/3.11 |
| 3,791,769 A | * | 2/1974 | Kovacs ........................ | 623/3.1 |
| 4,600,405 A | * | 7/1986 | Zibelin ........................ | 623/3.1 |
| 4,621,617 A | * | 11/1986 | Sharma ........................ | 623/3.1 |
| 5,344,443 A | * | 9/1994 | Palma et al. ................ | 623/3.14 |
| 5,895,421 A | * | 4/1999 | Nakhmanson ............... | 623/3.1 |
| 6,197,055 B1 | * | 3/2001 | Matthews .................... | 623/3.1 |
| 6,342,071 B1 | * | 1/2002 | Pless ........................... | 623/3.1 |

* cited by examiner

*Primary Examiner*—Danton D. DeMille
*Assistant Examiner*—Quang D. Thanh

(57) ABSTRACT

An artificial heart device for minimizing the damage to blood cells having electromagnetically driven pistons which move the blood around and through a toroidal chamber. In first and second preferred embodiments no motor is used to drive the pistons and the pistons are suspended within the toroid by cycling of electromagnets. In a third preferred embodiment the pistons are moved with the use of motor-driven magnets. In each embodiment blood is sucked into the toroidal chamber through one or more intake openings and blood exits the toroidal chamber through one or more outflow openings.

8 Claims, 8 Drawing Sheets

CIRCULAR ARTIFICIAL HEART

This application claims the benefit of Ser. No. 60/219,868, Jul. 20, 2000.

FIELD OF THE INVENTION

This invention relates to an implantable artificial heart for use in humans to take the place of a biological human heart. More particularly, the present invention provides a circular tube with sufficient openings for intake and output of blood wherein the blood is pumped by means of electromagnetically driven pistons.

BACKGROUND OF THE INVENTION

Implantable artificial heart, or ventricular assist, devices heretofore have been used primarily as temporary blood pumping mechanisms upon end-stage heart failure until such time as a donor human heart becomes available. There is a significant shortage of human heart donors, however, which requires a need for a long-term or permanent artificial heart device. Nevertheless, existing implantable artificial heart devices are not satisfactory for long-term or permanent use due to a variety of factors. A large number of such prior art devices utilize axial flow pumps which rely upon impellers to move the blood. The use of impellers has historically caused a great number of problems, including damage to the blood cells, non-uniform flow and stagnant areas in which clotting may occur. More recently, axial flow pumps have been developed in which the impeller is caused to turn within an electromagnetic field as opposed to the use of an electric motor. Such electromagnetically driven impellers generally still involve certain of the deficiencies of electrically driven impeller pumping systems, such as cell damage, non-uniform flow and stagnant areas.

SUMMARY OF THE INVENTION

It is an object of the present invention to provide a long-term or permanent implantable ventricular assist, or artificial heart device. The device of the present utilizes electromagnetically suspended and rotated pistons which move radially about a double walled tubular housing. In a first embodiment of the artificial heart, a two chambered housing is utilized, each chamber having one intake and one outflow openings and two electromagnetically driven and suspended pistons. Each chamber functions as a ventricle/auricle pair. A single chamber having two intake and two outflow openings and three electromagnetically driven and suspended pistons functions as two ventricle/auricle pairs in the second embodiment of the artificial heart.

DETAILED DESCRIPTION OF THE INVENTION

Figure 6:
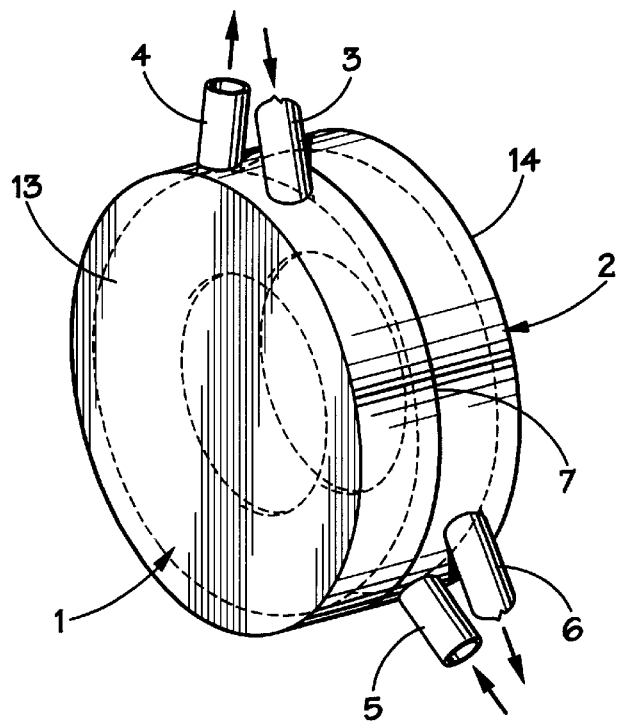
FIG. 6 shows a perspective view of a first preferred embodiment of the artificial heart.

Referring first to FIG. 6, an exterior view of a first preferred embodiment of the artificial heart is shown. The artificial heart is made of two chambers, a first chamber 1 and a second chamber 2. First chamber 1 has an intake opening 3 and an outflow opening 4. Second chamber 2 has an intake opening 5 and an outflow opening 6. First chamber 1 is separated from second chamber 2 by a solid dividing wall, the perimeter of which is shown in FIG. 6 as 7. First chamber 1 has an end plate 13. Second chamber 2 has an end plate 14.

Figure 1:
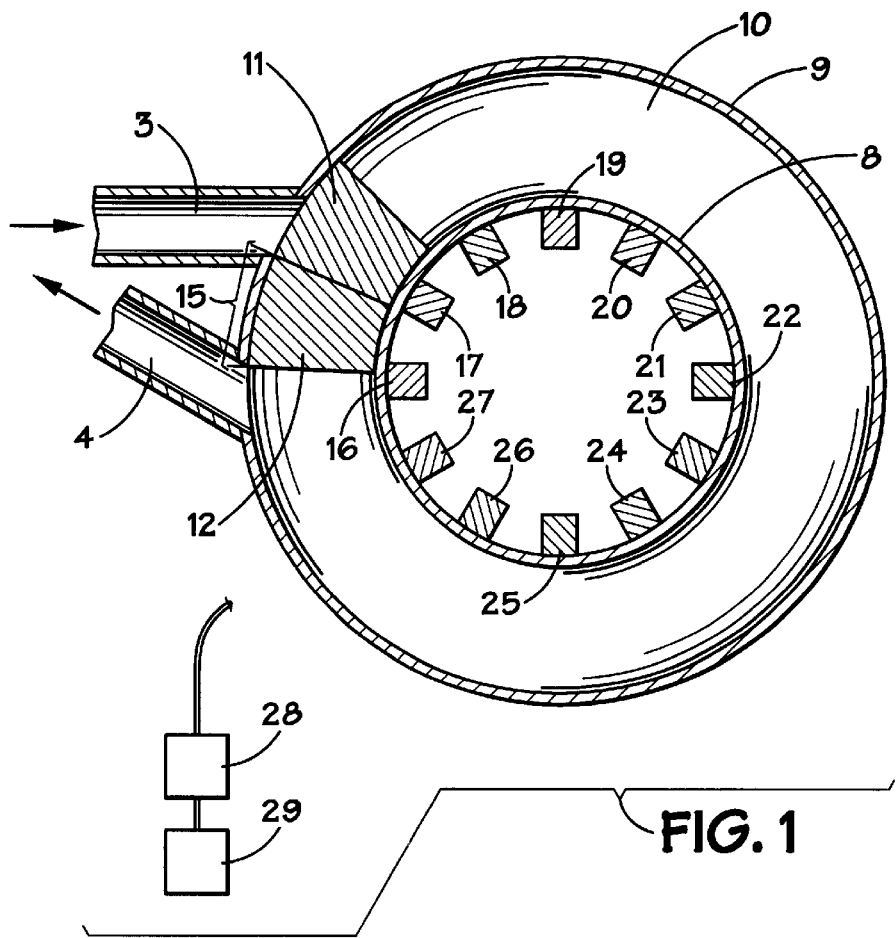
FIG. 1 is a cross sectional view of a first chamber of a first preferred embodiment of the circular artificial heart in a starting position of a cycle.

Referring now to FIG. 1, a cross section view of chamber 1 is shown. It will be understood that a cross section of chamber 2 would look identical to that of chamber 1. As seen in FIG. 1, chamber 1 is a double-walled tube forming a toroid, the inner wall 8 and outer wall 9 of the tube being concentric and spaced so as to form a internal radial aperture 10. Intake opening 3 and outflow opening 4 each communicate with aperture 10. Intake opening 3 and outflow opening 4 are separated along the outer wall 7 by a separation arc 15. A first piston 11 and a second piston 12, each subscribing an arc of about the same size as separation arc 15. Separation arc 15 is larger than the arc subscribed by the intersection of the larger of intake opening 3 or outflow opening 4 with aperture 10. Thus, each of pistons 11 and 12 will be larger than both of openings 3 and 4 so as to prevent the pistons from entering the outflow opening 4. First piston 11 is sized so as to fit within aperture 10 leaving a slight clearance between first piston 11 and the walls of aperture 10. Second piston 12 is sized so as to fit between within aperture 10 leaving no more than a slight clearance between second piston 12 and the walls of aperture 10. It will be understood that the size of the clearance between first and second pistons and the walls of aperture 10 are sized so as to minimize or prevent any potential backflow of blood while also preventing or minimizing friction caused by movement of the pistons.

Figure 14:
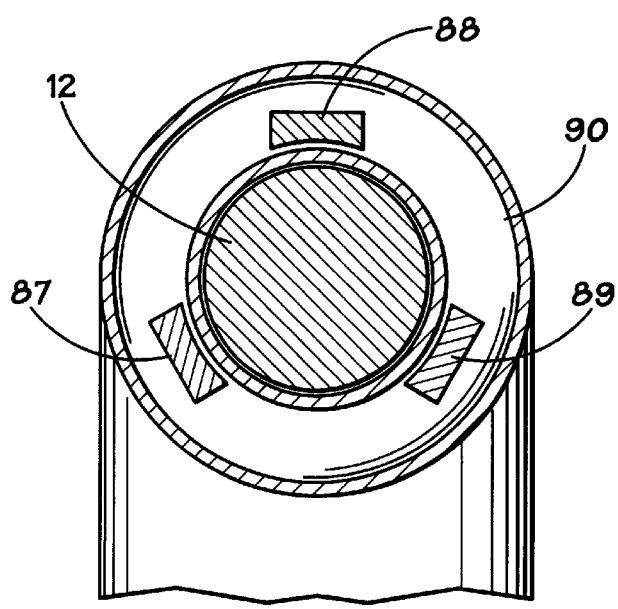
FIG. 14 is a cross sectional view of an electromagnet assembly used in the artificial heart.

A plurality of electromagnet assemblies lie along the exterior side of inner wall 8. In FIG. 1, the artificial heart is shown with twelve equally sized and spaced electromagnets, 16, 17, 18, 19, 20, 21, 22, 23, 24, 25, 26, and 27. Each of electromagnet assemblies 16–27 connects electrically to a control unit 28. Control unit 28 is electrically connected to and powered by a long-life battery 29. Each of electromagnet assemblies 16–27 may be turned on and off by control unit 28. Power may be supplied to electromagnet assemblies 16–27 by or through control unit 28. Control unit 28 and battery 29 preferably lie under the skin of the wearer of the circular artificial heart, as is typically done with pacemaker devices. Each of first piston 11 and second piston 12 are made wholly or partially of a magnetic material so as to be attracted to electromagnet assemblies 16–27 when such electromagnet assemblies are turned on and are magnetized. Referring now to FIG. 14 a cross section of a magnet is shown. Each electromagnet assembly 16–27 is actually a combination of three electromagnets of identical strength spaced equidistant from each other within a sheath. As shown in FIG. 14, the three component magnets 87, 88, and 89 are held within a toroidal sheath 90. The use of three equidistantly spaced and equally strong magnets allows the pistons to be levitated within the aperture eliminating or minimizing friction between the pistons and the inside surfaces of the outer wall and inner wall. All three component electromagnets of each of electromagnet assemblies 16–27 are controlled together. For example, when electromagnet assembly 17 is turned on, all three component electromagnets of electromagnet assembly 17 are turned on. It will be understood that a single or two electromagnets could be used in place of the three electromagnet assemblies but in such case pistons 11 and 12 would not be levitated within aperture 10 so as to reduce friction caused by the movement of pistons 11 and 12. Furthermore, it will be understood that more than three electromagnets could be used within each electromagnet assembly to achieve the same results as achieved with three electromagnets.

Referring still to FIG. 1, the starting position of a cycle of the artificial heart is shown. In the starting position, aperture 10 is filled with blood, first piston 11 is positioned so as to close off communication of intake opening 3 and aperture 10. Second piston 12 is positioned along separation arc 15. In the starting position, electromagnet assemblies 16 and 17 are turned on, with electromagnet assembly 16 holding second piston 12 in place and electromagnet assembly 17 holding first piston 11 in place.

Figure 2:
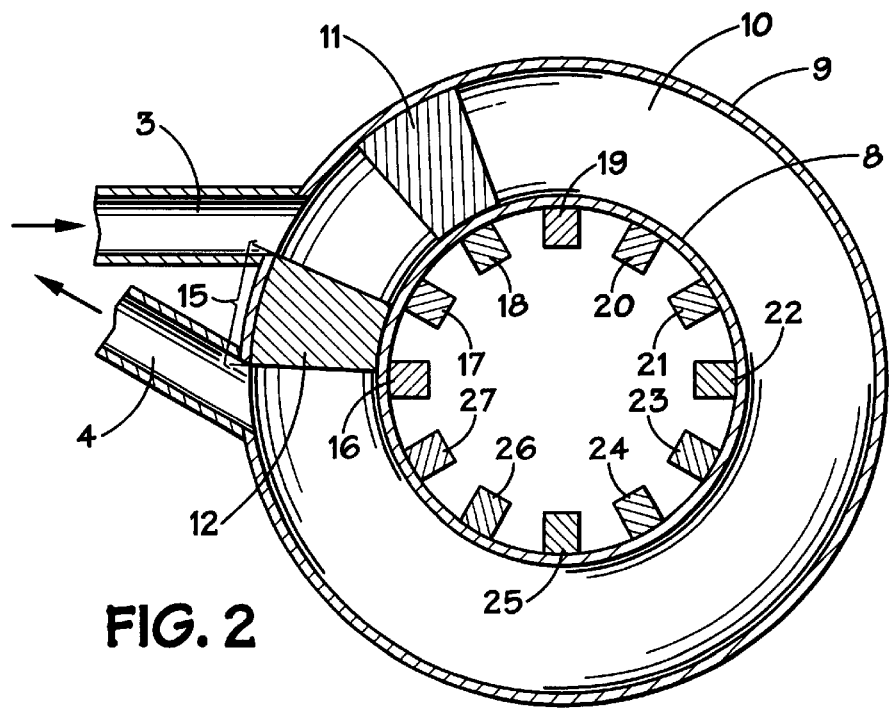
FIG. 2 shows the artificial heart of FIG. 1 in a second position of a cycle.
Figure 3:
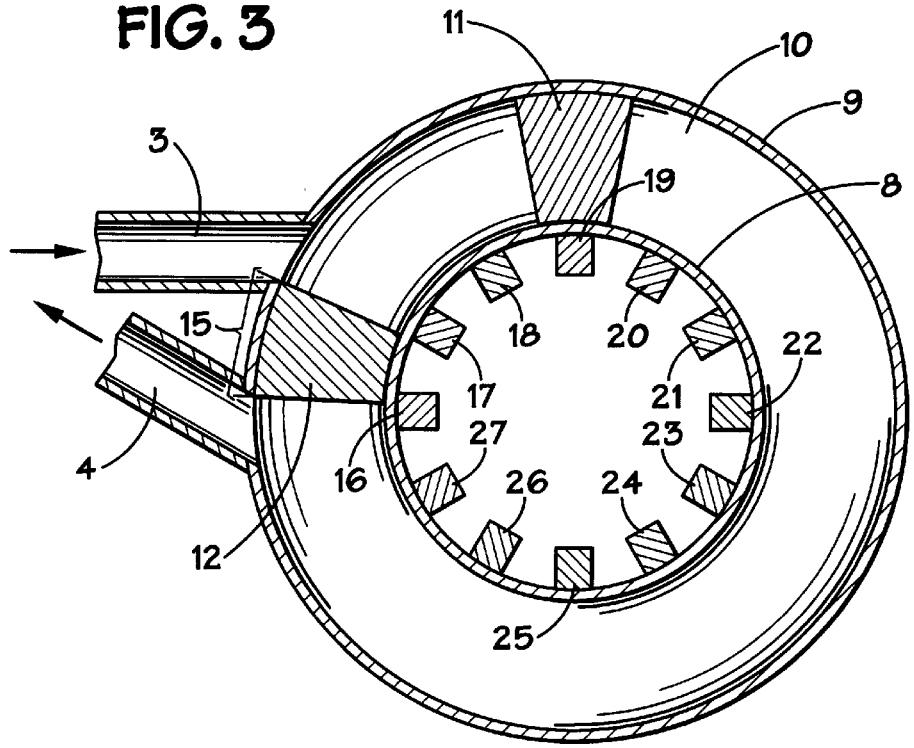
FIG. 3 shows the artificial heart of FIG. 1 in a third position of a cycle.
Figure 4:
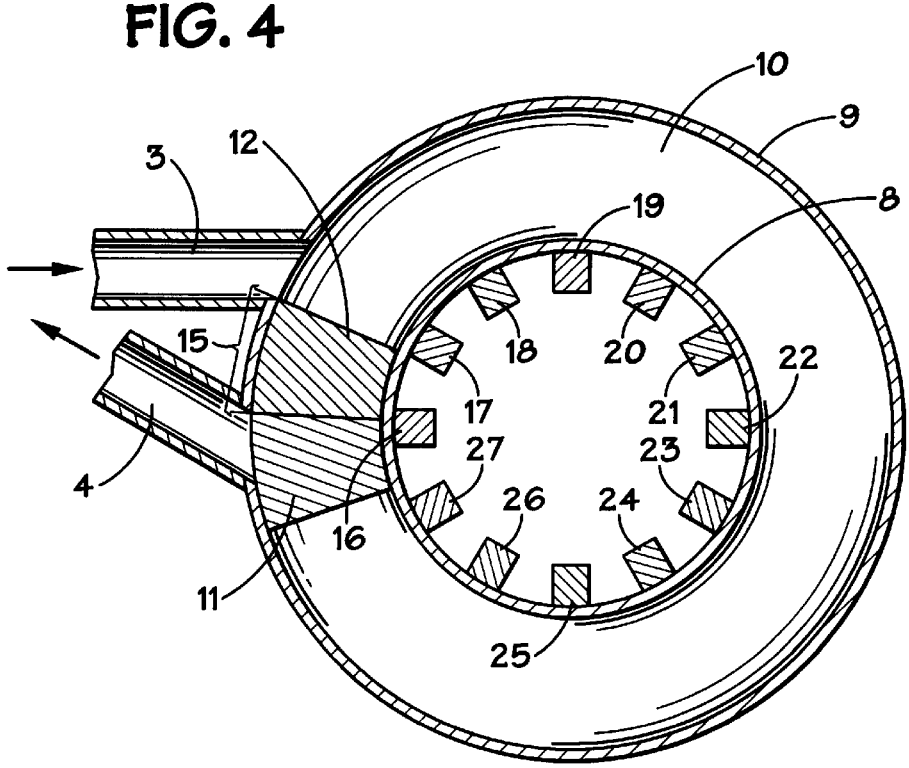
FIG. 4 shows the artificial heart of FIG. 1 in a near final position of a cycle.

To continue the cycle of the artificial heart, electromagnet assembly 17 is turned off and electromagnet assembly 18 is turned on. As shown in FIG. 2, first piston 11 is thereby attracted to electromagnet assembly 18 and moves radially along aperture 10, shown in a clockwise direction in FIG. 2. As shown in FIG. 3, electromagnet assembly 18 is then turned off and electromagnet assembly 19 is turned on thereby further moving first piston 11 radially along aperture 10. Although shown in discrete positions in FIGS. 1–3 for illustrative purposes, it will be understood that electromagnet assemblies 16–27 are cycled so as to provide a continuous and smooth movement of first piston 11 around aperture 10. While making its radial movement along aperture 10, first piston 11 pushes the volume of blood in aperture 10 forward and out of outflow opening 4. As first piston 11 moves along aperture 10, a vacuum is formed behind first piston 11 and blood flows in through intake opening 3 into aperture 10 behind first piston 11. Referring now to FIG. 4, the latter stages of a cycle are shown in which electromagnet assembly 27 is turned on and first piston 11 moves into a position in which first piston 11 temporarily blocks the communication between outflow opening 4 and aperture 10.

Figure 5:
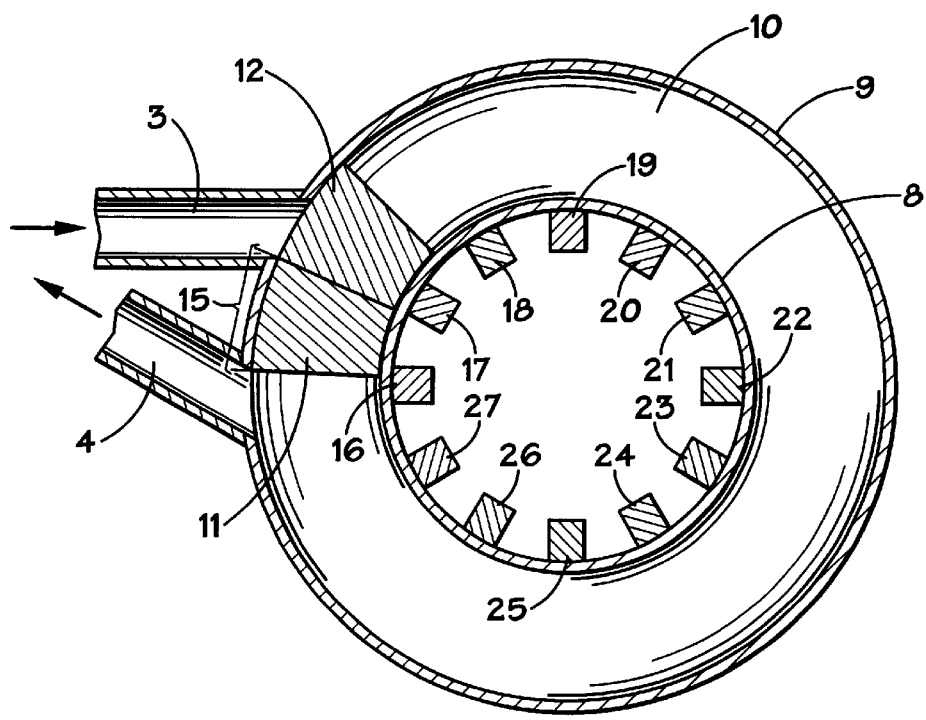
FIG. 5 shows the artificial heart of FIG. 1 in a final position of a cycle.

FIG. 5 illustrates a final position of a cycle of the artificial heart. As seen in FIG. 5, electromagnet assembly 16 is turned off and electromagnet assembly 17 is turned on thereby moving second piston 12 into a position to close the communication between aperture 10 and intake opening 3. Electromagnet assembly 27 is turned off and electromagnet assembly 16 is then turned on so as to move first piston 11 into a position along separation arc 15. The timing of turning electromagnet assemblies 16, 17 and 27 on and off is such that first piston 11 and second piston 12 do not butt against each other. A second cycle may then be begun with second piston 12 moving radially along aperture 10 and pushing the volume of blood out outflow opening 4.

The pumping action described in connection with FIGS. 1–5 is duplicated in second chamber 2. The pistons of first chamber 1 and second chamber 2 all move at a rate so as to pump about five quarts of blood per minute.

Figure 7:
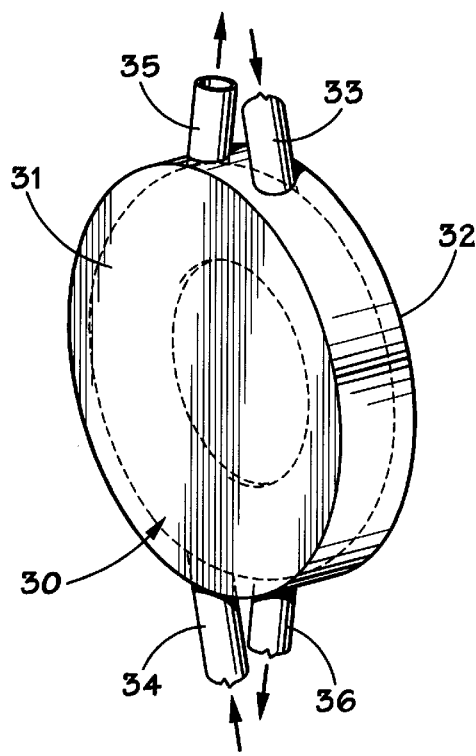
FIG. 7 shows a perspective view of a second preferred embodiment of the artificial heart.

Referring now to FIG. 7, an exterior perspective view of a second preferred embodiment of the artificial heart is shown. In the second embodiment, a single chamber 30 having two end plates 31 and 32, two intake openings 33 and 34 and two outflow openings 35 and 36 performs as two ventricle/auricle pairs. Each of openings 33–36 are substantially equal in diameter or width.

Figure 8:
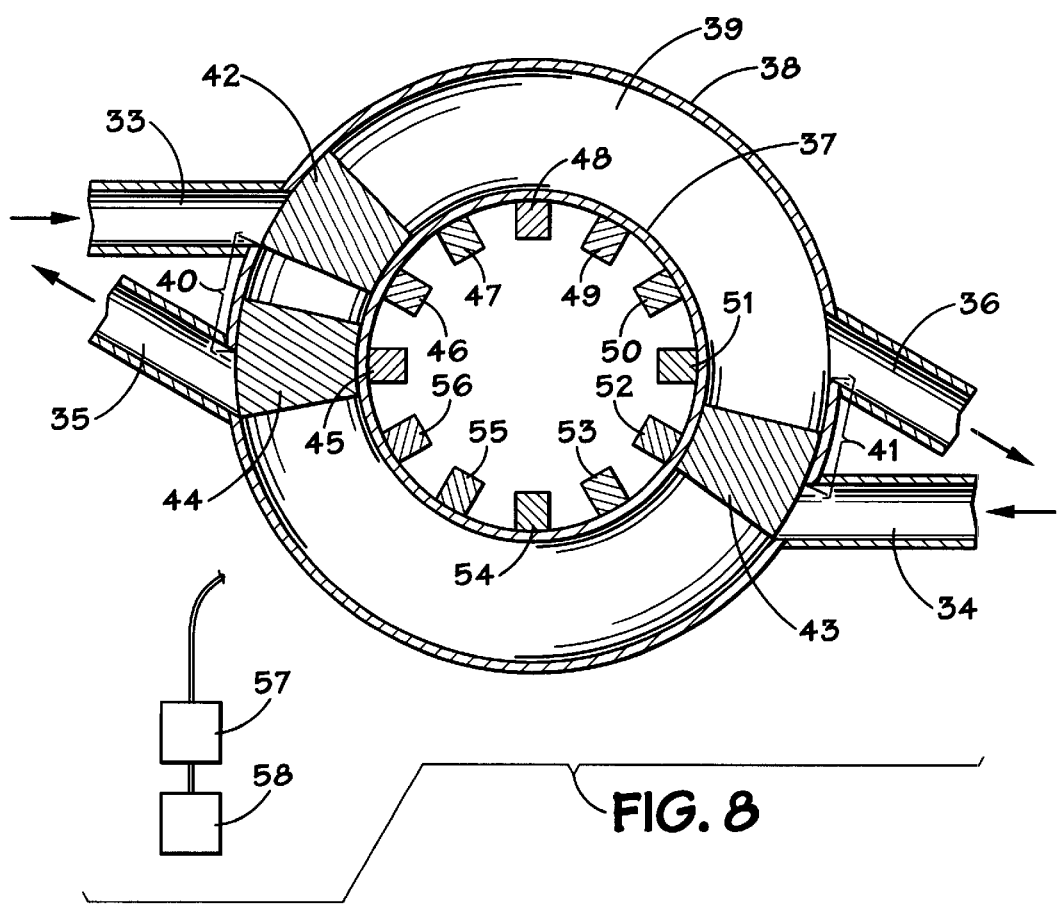
FIG. 8 is a c ross sectional view of the chamber of a second preferred embodiment of the circular artificial heart in a starting position of a first cycle.

Referring now to FIG. 8, it can be seen that chamber 30 is of the same shape and configuration as each of first chamber 1 and second chamber 2 of the first preferred embodiment. As seen in FIG. 8, chamber 30 is a double-walled tube, forming a toroid, the inner wall 37 and outer wall 38 of the tube being concentric and spaced so as to form an aperture 39. Intake openings 33 and 34 and outflow openings 35 and 36 each communicate with aperture 39. Intake opening 33 and outflow opening 35 are separated along the outer wall 38 by a separation arc 40. Intake opening 34 and outflow opening 36 are separated along the outer wall 38 by a separation arc 41. Separation arc 40 and 41 are essentially equal in size. Intake openings 33 and 34 are positioned at about 180 degrees apart from each other and outflow openings 35 and 36 are positioned at about 180 degrees apart from each other. A first piston 42, a second piston 43 and a third piston 44, each subscribing an arc of a size equal to about one half the size of separation arc 15 plus the width of openings 33. First piston 42, second piston 43 and third piston 44 are sized so as to fit within aperture 39 leaving a slight clearance between each piston and the walls of aperture 39. The size of the clearance between pistons 42, 43 and 44 and the walls of aperture 39 are sized so as to minimize or prevent any potential backflow of blood while also preventing or minimizing friction caused by movement of the pistons.

A plurality of electromagnet assemblies lie along the exterior side of inner wall 37. In FIG. 8, the artificial heart is shown with twelve equally sized and spaced electromagnet assemblies, 45–56. Each of electromagnet assemblies 45–56 connects electrically to a control unit 57. Control unit 57 is electrically connected to and powered by a long-life battery 58. Each of electromagnet assemblies 45–56 may be turned on and off by control unit 57. Power may be supplied to electromagnet assemblies 45–56 by or through control unit 57. Control unit 57 and battery 58 preferably lie under the skin of the wearer of the circular artificial heart, as is typically done with pacemaker devices. Each of first piston 42, second piston 43 and third piston 44 are made wholly or partially of a magnetic material so as to be attracted to electromagnet assemblies 45–56 when such electromagnets are turned on and are magnetized. Referring now to FIG. 14 a cross section of a electromagnet assembly is shown. Each electromagnet assembly 45–56 is actually a combination of three electromagnets of identical strength spaced equidistant from each other within a toroidal sheath. As shown in FIG. 14, the three component magnets 87, 88, and 89 are held within a toroidal sheath 90. The use of three equidistantly spaced and equally strong electromagnets allows the pistons to be levitated within the aperture eliminating or minimizing friction between the pistons and the inside surfaces of the outer wall and inner wall. All three component electromagnets of each of electromagnet assembly 45–56 are controlled together. For example, when electromagnet assembly 46 is turned on, all three component electromagnets of electromagnet assembly 46 are turned on. It will be understood that a single or two electromagnets could be used in place of each electromagnet assembly 45–56 but in such case, the pistons would not be levitated within aperture 39 so as to further minimize friction caused by the movement of the pistons. It will be further understood that more than three electromagnets could be used in each electromagnet assembly with the same results.

Referring to FIG. 8, the starting position of a cycle of the artificial heart is shown. In the starting position, aperture 39 is filled with blood, first piston 42 is positioned so as to close off communication of intake opening 33 and aperture 39. Third piston 44 is positioned so as to close off communication of outflow opening 35 with aperture 39 and slightly underlying separation arc 40. Second piston 43 is positioned so as to close off communication of intake opening 34 and aperture 39 and slightly underlying separation arc 41. In the starting position, electromagnet assemblies 45, 46 and 52 are turned on, with electromagnet assembly 45 holding third piston 44 in place, electromagnet assembly 46 holding first piston 42 in place and electromagnet assembly 52 holding second piston 43 in place.

Figure 9:
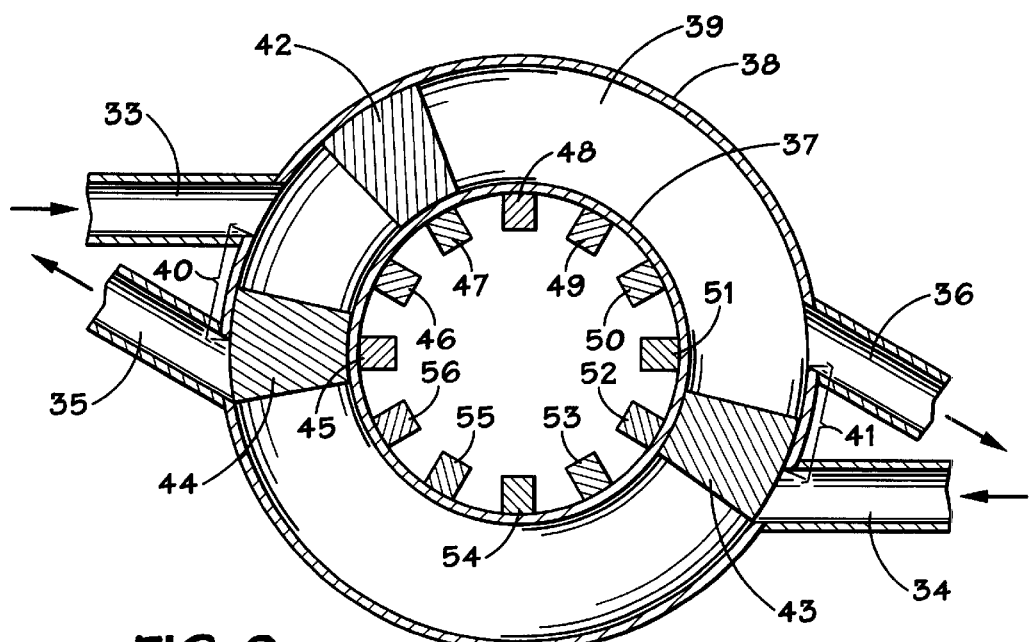
FIG. 9 shows the artificial heart of FIG. 8 in a second position of a first cycle.
Figure 10:
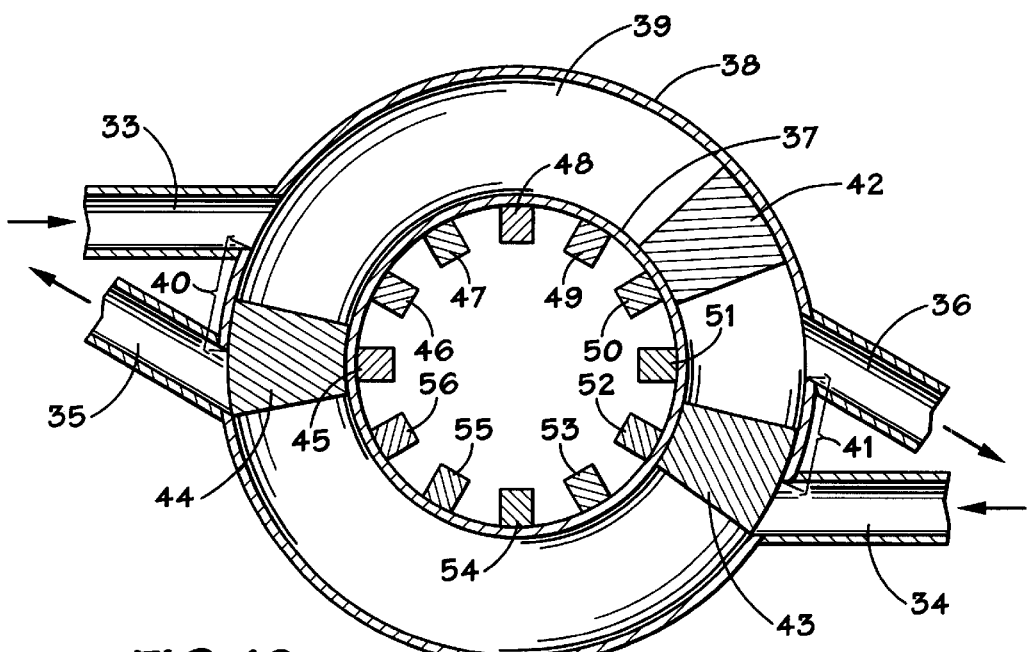
FIG. 10 shows the artificial heart of FIG. 8 in a third position of a first cycle.
Figure 11:
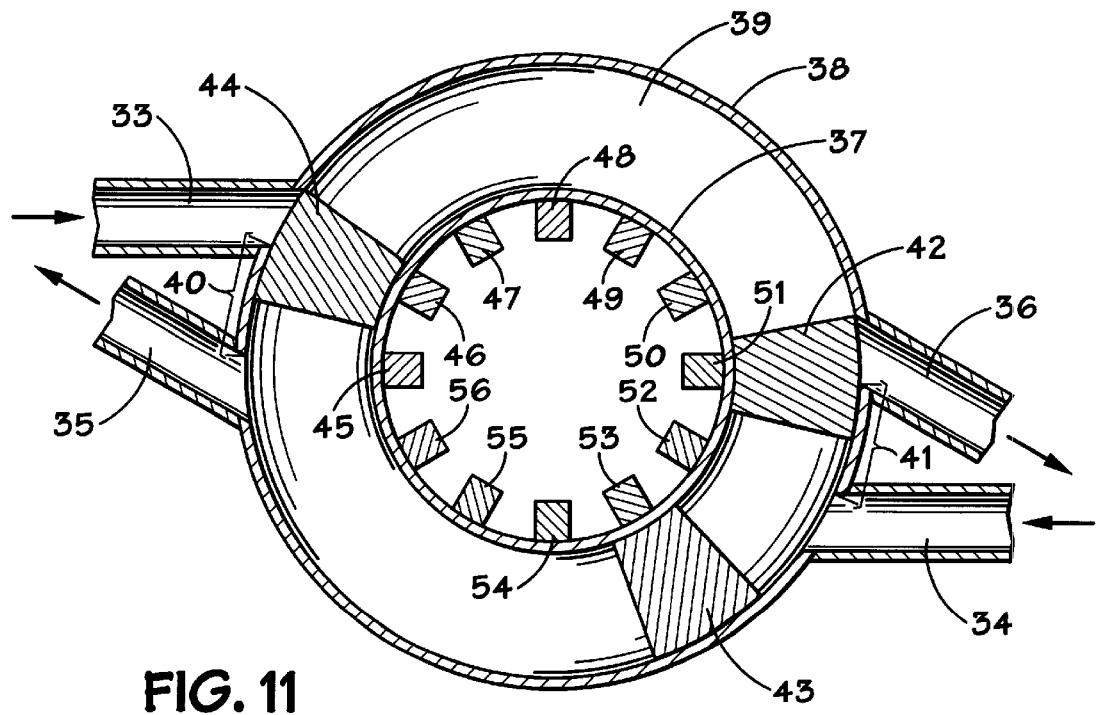
FIG. 11 shows the artificial heart of FIG. 8 in a final position of a first cycle and a starting position of a second cycle.

To continue the cycle of the artificial heart, electromagnet assembly 46 is turned off and electromagnet assembly 47 is turned on. As shown in FIG. 9, first piston 42 is thereby attracted to electromagnet assembly 47 and moves radially within aperture 39, shown in a clockwise direction in FIG. 9. Cycling of electromagnet assemblies 47–50 sequentially causes the radial movement of first piston 42 to continue. As seen in FIG. 10, electromagnet assembly 50 is turned on causing first piston 42 to move within aperture 39 until it is held in place by electromagnet assembly 50. Although shown in discrete positions in FIGS. 8–10 for illustrative purposes, it will be understood that electromagnet assemblies 46–50 are cycled so as to provide a continuous and smooth movement of first piston 42 through aperture 39. While making its radial movement through aperture 39, first piston 42 pushes the volume of blood in aperture 39 forward and out of outflow opening 36. As first piston 42 moves through aperture 39, a vacuum is formed behind first piston 42 and blood flows in through intake opening 33 into aperture 39 behind first piston 42. Referring now to FIG. 11, electromagnet assembly 52 is turned off and electromagnet assembly 53 is turned on thereby causing second piston 43 to move through aperture 39 toward outflow opening 35. Essentially simultaneously, electromagnet 50 is turned off and electromagnet assembly 51 is turned on causing first piston 42 to block off communication of outflow opening 36 with aperture 39. Essentially simultaneously, electromagnet assembly 45 is turned off and electromagnet 46 is turned on thereby moving third piston 44 through aperture 39 so as to block communication of intake opening 33 with aperture 39. Upon positioning of first piston 42 along outflow opening 36, a first cycle is completed. That is, that portion of chamber 30 between intake opening 33 and outflow opening 36 functions as one auricle/ventricle pair. As will be seen that portion of chamber 30 between intake opening 34 outflow opening 35 functions as a second auricle/ventricle pair.

Figure 12:
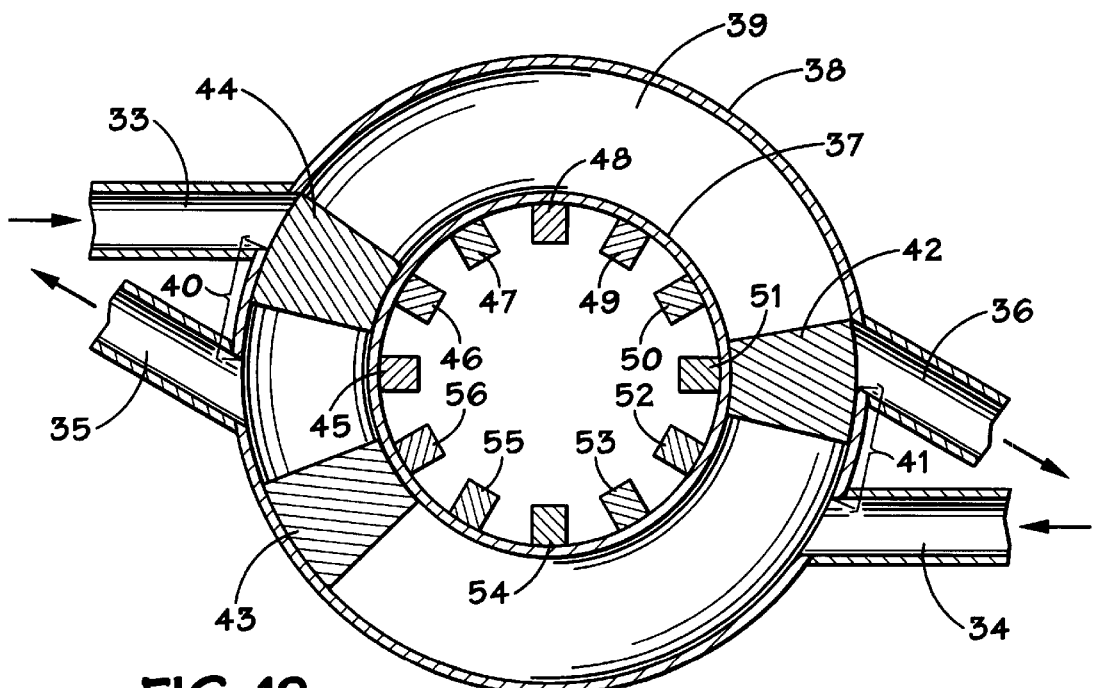
FIG. 12 shows the artificial heart of FIG. 8 in a near final position of a second cycle.
Figure 13:
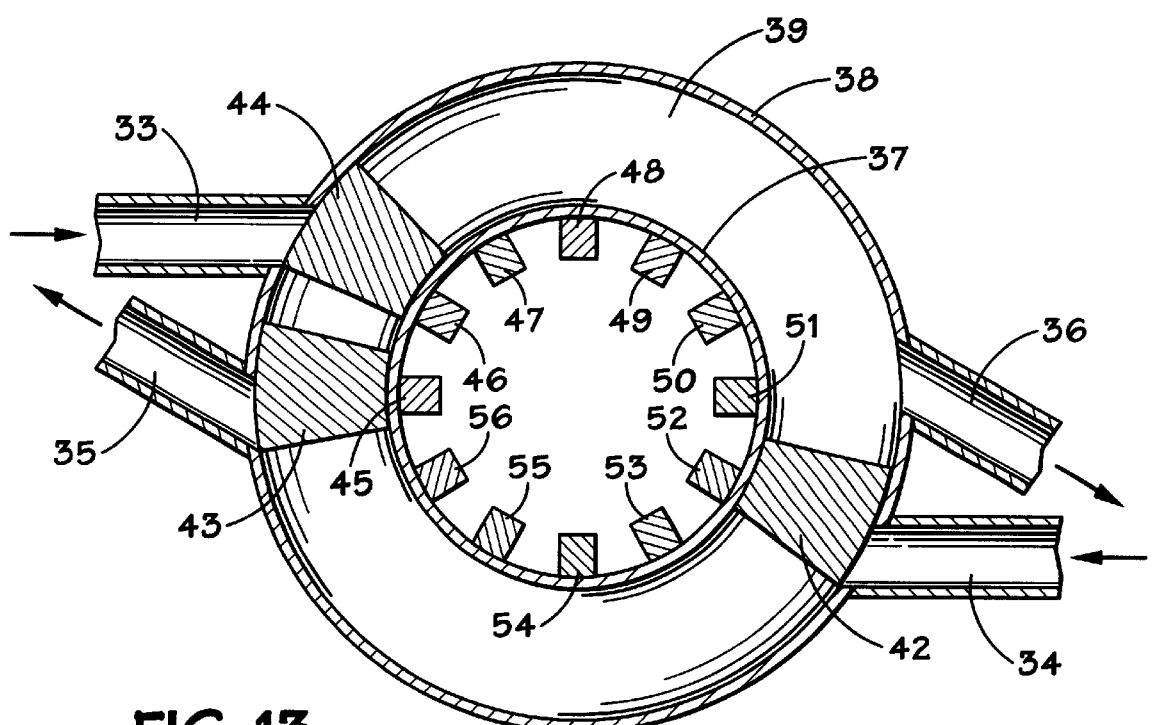
FIG. 13 shows the artificial heart of FIG. 8 in a final position of a second cycle and a starting position of a third cycle.

Referring now to FIG. 12, second piston 43 has moved further through aperture 39 by cycling of electromagnet assemblies 52–56. As second piston 43 moves through aperture 39, second piston 43 pushes the blood in front of second piston 43 forward and out through outflow opening 35. Furthermore, as second piston 43 moves forward a vacuum is created behind second piston 43 and blood is sucked into aperture 39 through intake opening 34. FIG. 13 illustrates a final position of the second cycle of the artificial heart. As seen in FIG. 13, electromagnet assembly 56 is turned off and electromagnet assembly 45 is turned on thereby moving second piston 43 into a position to close the communication between aperture 39 and intake opening 35. The following cycle begins with movement of third piston 44 through aperture 39 by turning off electromagnet assembly 46 and turning on electromagnet assembly 47. The timing of turning electromagnet assemblies 45–56 on and off, or cycling, is such that first piston 42, second piston 43, and third piston 44 do not butt against each other at any point of any cycle.

Figure 15:
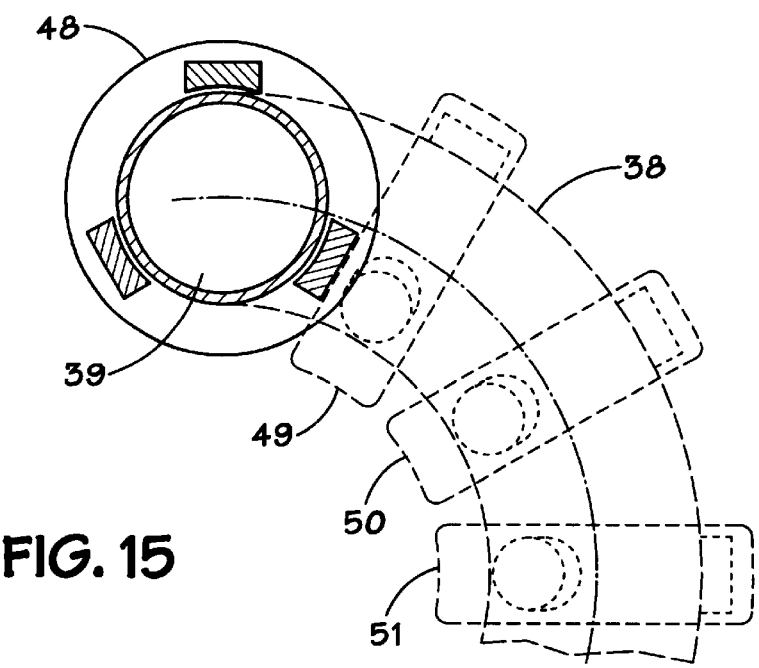
FIG. 15 is a partial cross section taken along line A—A in FIG. 8 of a second preferred embodiment of the circular artificial heart.

Referring now to FIG. 15, the manner in which the electromagnet assemblies 45–56 encircle or wrap around the outside of chamber 30 is shown. The electromagnetic assemblies similarly encircle or wrap around each of the two chambers in the first preferred embodiment.

Figure 16:
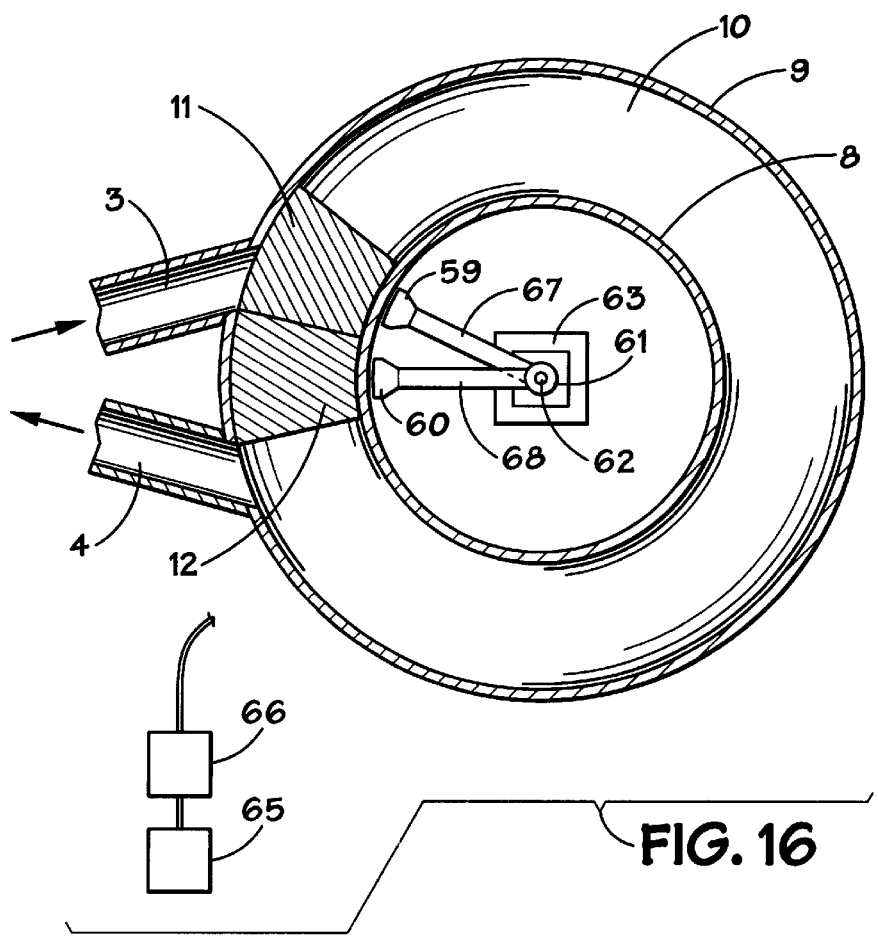
FIG. 16 is a cross sectional view of a third preferred embodiment of the circular artificial heart having two chambers.

Referring now to FIG. 16, a third preferred embodiment of the artificial heart is described. The third preferred embodiment has first and second chambers, 1 and 2, first and second pistons, 11 and 12, aperture 10, intake opening 3, outflow opening 4, outer wall 9, inner wall 8, and separation arc 15, as in the first preferred embodiment described in connection with FIGS. 1–6. In contrast to the first preferred embodiment, the third preferred embodiment utilizes a first arm 67 and a second arm 68, each arm having two ends, a first end being strongly magnetized 59 and 60, and a second end attached to a drive shaft 61 and 62 of a motor 63. Motor 63 is placed substantially at the center point of the circle formed by the exterior surface of inner wall 8. Each of arms 67 and 68 are substantially of the same length and are sufficiently long to extend from drive shafts 61 and 62 respectively to a distance close to inner wall 8. It will be understood that magnetized ends 59 and 60 of arms 67 and 68 respectively may be either magnetized portions of the respective arms or may be separate magnets attached fixedly to the end of the respective arms. Motor 63 is electrically connected to a power source 64 which is shown in FIG. 16 as a battery 65. Motor 63 is programmed to run according to instructions given by a control unit 66 which is electrically connected to motor 63. Pistons 11 and 12 are moved through aperture 10 by controlled rotation of arms 67 and 68 and the magnetized ends 59 and 60. Because each of pistons 11 and 12 move independently, each of arms 67 and 8 are placed on a separate drive shaft. Drive shafts 61 and 62 are independently controlled by motor 63 and may be placed concentrically with one drive shaft in the form of a hollow tube, as is well known in the field of clocks and watches, or, alternatively, drive shafts 61 and 62 may extend from opposite ends of motor 63. It will be understood that motor 63 may be constructed of two separate motors placed in a single motor housing and each connected electrically to battery 65 and to control unit 66. As shown in FIG. 16, the third preferred embodiment is in a starting position of a cycle.

A fourth preferred embodiment utilizes the single chamber design of the second preferred described in connection with FIGS. 7–13 herein and the motor driven magnetized arm means described in the third preferred embodiment in connection with FIG. 16. It will be understood that in the third preferred embodiment, three magnetized arms must be utilized to drive the three pistons, and therefore, three separate and independently controlled drive shafts are utilized.

Referring now to FIGS. 1–13, and 16 it can be seen that in the preferred embodiments, each intake opening 3, 33, and 34 is slanted such that blood flowing into the aperture through the intake opening flows in the general direction in which the blood will flow within the aperture. That is, each of the intake opening are slanted at an acute angle with the angle of interception between the outer wall of the chamber and the intake opening facing away from the direction of blood flow. As the angle decreases, there is a reduction in the turbulence and possible damage to the blood cells, in the inflowing blood stream. Although the intake openings may be placed at substantially ninety degrees to a tangent of the outer wall, such a placement is not used in the preferred embodiments, as it could cause turbulent flow, stagnant areas of little or no blood flow and damage to the blood cells. Similarly, to reduce turbulent flow, stagnant areas and damage to the blood cells, each outflow opening 4, 34 and 35 are also slanted such that blood flowing out of the artificial heart device continues to flow in the general direction that it was moving through the aperture as it flows out of the aperture.

Pistons 11, 12, 42, 43 and 44 are each in form of a partial toroid so as to fit within the aperture of the artificial heart device. Each of piston 11, 12, 42, 43, and 44 may be fitted with a gasket surrounding the piston and lying between the piston and the walls of the aperture. Alternatively, each of pistons 11, 12, 42, 43, and 44 may be coated, either partially or wholly, with a low friction material, such as Teflon, in which case, the coated piston may abut up against the walls of the aperture.

It will be understood that other features, such as sensory feedback and exertion dependent controls could be used in connection with the artificial heart of the present invention. For example, it is desirable in certain circumstances that the rate of blood pumping be variable, increasing with increasing exertion and decreasing during resting periods. Feedback systems which sense the level exertion or other relevant parameters and which then determine blood flow requirements through process of stored algorithms are currently available and under development. Such feedback systems could be added to the present invention without impeding the functioning of the circular artificial heart.

It will be further understood that the dimensions of the chambers, apertures, intake openings, and outflow openings may vary to optimize blood flow as appropriate to mimic the action of a natural heart and the functioning of a natural heart. Furthermore, it will be understood that although twelve equidistant electromagnet assemblies are shown in connection with the description of the first and second preferred embodiments herein, the location, number and types of magnets may vary to optimize the size and functioning of the circular artificial heart.

The circular artificial heart of the present invention may be constructed of any biocompatible material, including a wide range of polymeric materials and titanium, with the exception of those components which must be of magnetic materials are electrically conducting materials. The material of construction of those components which come into contact with the body or body fluids must, most importantly, be materials which minimize wearer rejection and blood clotting.

We claim:

1. A circular artificial heart device comprising:
    a first toroidal chamber having an outer wall and an inner wall, said inner and outer walls defining a first aperture and having a first outflow openings, said first outflow opening extending outward from an exterior surface of said outer wall and communicating with said first aperture, and having a first intake opening, said first intake opening extending outward from said exterior surface of said outer wall and communicating with said first aperture;
    said first intake opening and said first outflow opening separated along said outer wall by a first separation arc, said first separation arc larger than an arc subscribed by the larger of said first intake opening and said first outflow opening;
    a second toroidal chamber having an outer wall and an inner wall, said inner and outer walls defining a second aperture and having a second outflow opening, said second outflow opening extending outward from an exterior surface of said outer wall and communicating with said second aperture, and having a second intake opening, said second intake opening extending outward from said exterior surface of said outer wall and communicating with said second aperture;
    said second intake opening and said second outflow opening separated along said outer wall by a second separation arc, said second separation arc larger than an arc subscribed by the larger of said second intake opening and said second outflow opening;
    a first set of a plurality of electromagnet assemblies, each said electromagnet assembly comprising three electromagnets of substantially equal strength and located substantially equidistant from each other in a toroidal configuration perpendicularly about said first toroidal chamber;
    a first piston and a second piston in the shape of a partial toroid and each subscribing an arc of about the same size of said first separation arc, said first and second pistons positioned within said first aperture;
    a second set of a plurality of electromagnet assemblies, each said electromagnet assembly comprising three electromagnets of substantially equal strength and located substantially equidistant from each other in a toroidal configuration perpendicularly about said second toroidal chamber; and
    a third piston and a fourth piston in the shape of a partial toroid and each subscribing an arc of about the same size of said second separation arc, said third and fourth pistons positioned within said second aperture.

2. The circular artificial heart device of claim 1 further comprising programmable microprocessor means electrically connected to said electromagnet assemblies.

3. The circular artificial heart device of claim 1 further comprising battery means electrically connected to said electromagnet assemblies.

4. The circular artificial heart device of claim 1 further comprising sensor means electrically connected to said microprocessor means, said sensor means capable of recording a plurality of physical parameters of a wearer of said artificial heart device.

5. The circular artificial heart device of claim 1 wherein said first intake opening is sized compatibly with a human vena cava.

6. The circular artificial heart device of claim 1 wherein said first outflow opening is sized compatibly with a human aorta.

7. The circular artificial heart device of claim 1 wherein said second intake opening is sized compatibly with a human pulmonary vein.

8. The circular artificial heart device of claim 1 wherein said second outflow opening is sized compatibly with a human pulmonary aorta.

* * * * *

UNITED STATES PATENT AND TRADEMARK OFFICE
CERTIFICATE OF CORRECTION

| | | |
|---|---|---|
| PATENT NO. | : 6,576,010 B2 | Page 1 of 1 |
| APPLICATION NO. | : 09/909614 | |
| DATED | : June 10, 2003 | |
| INVENTOR(S) | : Izaak A. Ulert and Heinrich Lang | |

It is certified that error appears in the above-identified patent and that said Letters Patent is hereby corrected as shown below:

TITLE PG. ITEM (76) INVENTORS; DELETE "MEINRICH" AND INSERT

--HEINRICH--.

Signed and Sealed this

Twelfth Day of February, 2008

JON W. DUDAS
*Director of the United States Patent and Trademark Office*